United States Patent [19]

Gupta

[11] Patent Number: 4,714,781

[45] Date of Patent: * Dec. 22, 1987

[54] PROCESS FOR PRODUCING 4-RING-SUBSTITUTED PHENYL LOWER ALKYL KETONES

[75] Inventor: Balaram B. G. Gupta, North Plainfield, N.J.

[73] Assignee: Hoechst Celanese Corporation, Somerville, N.J.

[*] Notice: The portion of the term of this patent subsequent to May 26, 2004 has been disclaimed.

[21] Appl. No.: 844,641

[22] Filed: Mar. 27, 1986

[51] Int. Cl.[4] .............................................. C07C 45/46
[52] U.S. Cl. ..................................................... 568/319
[58] Field of Search ......................................... 568/319

[56] References Cited

U.S. PATENT DOCUMENTS

| | | | |
|---|---|---|---|
| 3,354,221 | 11/1967 | Landis | 568/310 |
| 3,702,886 | 8/1973 | Argauer | 260/668 R |
| 4,061,724 | 9/1978 | Grose et al. | 585/467 |
| 4,285,919 | 7/1981 | Klotz | 585/467 |

OTHER PUBLICATIONS

Olah, "Freidel–Crafts and Related Reactions", vol. III, pp. 36–49 (1964).

*Primary Examiner*—James H. Reamer
*Attorney, Agent, or Firm*—Marvin Turken

[57] ABSTRACT

The production of a 4-lower alkyl or 4-phenyl ring-substituted phenyl lower alkyl ketone, e.g. 4-methylacetophenone, 4-ethylacetophenone or 4-phenylacetophenone, is carried out by reacting a lower alkyl- or phenyl-substituted benzene, e.g. toluene, ethylbenzene, or biphenyl, with a lower alkanoic acid, e.g. acetic acid, at an elevated temperature in the presence of a medium pore, pentasil-type molecular sieve, e.g. an H-ZSM-5 zeolite, a silicalite or an AMS-1B borosilicate, as catalyst.

20 Claims, No Drawings

PROCESS FOR PRODUCING 4-RING-SUBSTITUTED PHENYL LOWER ALKYL KETONES

This invention relates to a process for producing 4-lower alkylphenyl lower alkyl ketones such as 4-methylacetophenone or 4-phenyl phenyl lower alkyl ketones such as 4-phenyl acetophenone.

BACKGROUND OF THE INVENTION

Compounds such as 4-lower alkyl- or 4-phenyl-substituted phenyl lower alkyl ketones, e.g. 4-methylacetophenone (4-MAP) are possible intermediates for a variety of products having different end uses. Thus 4-MAP may be converted into para-cresol (4-methyl phenol) by first reacting the 4-MAP to form the monoacetate ester of para-cresol using a "Baeyer-Villiger" oxidation as disclosed, for example in application Ser. No. 661,552, filed Oct. 17, 1984 and the references cited therein, and then converting the monoacetate ester to para-cresol by hydrolysis, e.g. as disclosed in the previously cited application Ser. No. 661,552, or by transesterification as disclosed in Ser. No. 689,533, filed Jan. 7, 1985 and the references cited therein. The 4-MAP can also be convered into 4-hydroxybenzoic acid (4-HBA) by obtaining the monoacetate ester of para-cresol by the Baeyer-Villiger oxidation as described, oxidizing the methyl group by conventional means to form the corresponding acetate ester of 4-HBA and hydrolyzing the latter compound as described to obtain the 4-HBA.

Simons et al, Journal of the American Chemical Society, 61, 1795 and 1796 (1939) teach the acylation of aromatic compounds using hydrogen fluoride as a condensing agent and in Table 1 on page 1796 show the acetylation of toluene with acetic acid to produce p-methylacetophenone (4-MAP).

Various zeolites and zeolites-type materials are known in the art for the catalysis of chemical reactions. For example, U.S. Pat. No. 3,702,886, of Argauer, discloses a class of synthetic zeolites, characterized as "Zeolite ZSM-5", which are effective for the catalysis of various hydrocarbon conversion processes.

U.S. Pat. No. 4,061,724 of Grose et al disclose various synthetic crystalline silica polymorphs or "silicalites" which are stated to be useful in selectively adsorbing organic materials from water.

U.S. Pat. No. 4,285,919 of Klotz et al disclose certain crystalline borosilicates, i.e. "AMS-1B" borosilicates which are stated to be useful as catalysts for various hydrocarbon conversion processes.

U.S. Pat. No. 3,354,221 of Landis et al disclose the use of various crystalline aluminosilicate zeolites as catalysts for the Fries rearrangement of phenolic esters to hydroxy aromatic ketones.

Applicant's pending application Ser. No. 803,194, filed Dec. 2, 1985, teaches the use of ZSM-5 zeolites as catalysts for the reaction of phenol and a lower alkanoic acid, e.g. acetic acid, to form 2-hydroxyphenyl lower alkyl ketone such as 2-hydroxyacetophenone.

Pending application Ser. No. 803,195, filed Dec. 2, 1985 by Nicolau et al, teaches the use of silicalites as catalysts for reactions similar to those disclosed in application Ser. No. 803,194 described in the preceding paragraph.

SUMMARY OF THE INVENTION

In accordance with this invention, a lower alkyl- or phenyl substituted benzene, e.g. toluene, ethylbenzene or biphenyl, is reacted with a lower alkanoic acid, e.g. acetic acid, in the presence of a medium-pore, pentasil-type molecular sieve, to produce a 4-lower alkyl- or 4-phenyl ring-substituted phenyl lower alkyl ketone, e.g. 4-methylacetophenone (4-MAP), 4-ethylacetophenone (4-EAP), or 4-phenylacetophenone (4-PAP).

DESCRIPTION OF SPECIFIC EMBODIMENTS

The reaction between the lower alkyl- or phenyl-substituted benzene and the lower alkanoic acid proceeds in accordance with the following equation:

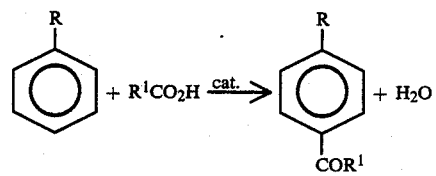

where R is lower alkyl, e.g. containing 1 to 3 carbon atoms, or phenyl, and $R^1$ is lower alkyl, e.g. containing 1 to 3 carbon atoms and may be the same as or different from R. R and $R^1$ may separately be, for example, methyl, ethyl, n-propyl or isopropyl.

If the substituted benzene is toluene, i.e. R is methyl and the lower alkanoic acid is acetic acid, i.e. $R^1$ is also methyl, the reaction proceeds as in the following equation:

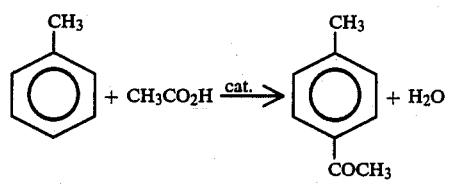

As stated, the catalyst for the reaction is a medium pore, pentasil-type molecular sieve. In general, such catalysts are crystalline silicates containing a configuration of linked tetrahedra consisting of eight of twelve five-membered rings and a channel system which is three-dimensional and defined by somewhat elliptical ten-membered rings of tetrahedra, and consists of intersecting straight and sinusoidal channels. Many of the silicates contemplated as catalysts under this invention have pores in the range of about 5 to 8 Angstrom units in diameter. Moreover, they often have similar although not necessarily identical X-ray diffraction patterns but have at least the following significant lines (i.e. interplanar spacings) in Table I, wherein "s"=strong, "w"=weak, "v.s."=very strong, and "m"=medium:

TABLE I

| Interplanar Spacing d(A) | Relative intensity |
|---|---|
| 11.2 ± 0.2 | w-vs |
| 10.0 ± 0.2 | w-vs |
| 6.04 ± 0.1 | w-m |
| 5.97 | |
| 3.82 ± 0.1 | vs |
| 3.7 ± 0.05 | ms-s |
| 2.99 ± 0.02 | w-m |

One class of pentasil type catalysts contemplated under this invention are the H-ZSM-5 zeolites of which are prepared by replacing with hydrogen ions most of the cations of a ZSM-5 zeolite, the composition, charateristics and preparation of which are set out in the previously cited U.S. Pat. No. 3,702,886 of Argauer, the entire disclosure of which is incorporated by reference. These ZSM-5 zeolites have the following formula:

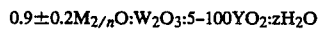

$0.9 \pm 0.2 M_{2/n}O : W_2O_3 : 5\text{--}100 YO_2 : zH_2O$ wherein M is a cation, n is the valence of said cation, W is selected from the group consisting of aluminum and gallium, Y is selected from the group consisting of silicon and germanium, and z is from 0 to 40. In a preferred synthesized form, the zeolite has a formula, in terms of mole ratios of oxides, as follows:

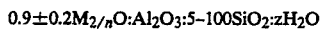

$0.9 \pm 0.2 M_{2/n}O : Al_2O_3 : 5\text{--}100 SiO_2 : zH_2O$ and M is selected from the group consisting of a mixture of alkali metal cations, especially sodium, and tetraalkyl-ammonium cations, the alkyl groups of which preferably contain 2–5 carbon atoms. In a particularly preferred class of catalysts for purposes of the present invention, the molar ratio of $SiO_2$ to $Al_2O_3$ in the latter formula is within the ratio of about 20 to 60.

The ZSM-5 zeolites in most cases have a distinguishing crystalline structure yielding an X-ray diffraction pattern determined as described in U.S. Pat. No. 2,702,886, with significant lines as indicated in Table II, wherein "s"=strong, "w" weak and "v.s."=very strong.

TABLE II

| Interplanar Spacing d(A) | Relative intensity |
|---|---|
| 11.1 ± 0.2 | s. |
| 10.0 ± 0.2 | s. |
| 7.4 ± 0.15 | w. |
| 7.1 ± 0.15 | w. |
| 6.3 ± 0.1 | w. |
| 6.04 ± 0.1 | w. |
| 5.97 | |
| 5.56 ± 0.1 | w. |
| 5.01 ± 0.1 | w. |
| 4.60 ± 0.06 | w. |
| 4.25 ± 0.06 | w. |
| 3.85 ± 0.07 | v.s. |
| 3.71 ± 0.05 | s. |
| 3.04 ± 0.03 | w. |
| 2.99 ± 0.02 | w. |
| 2.94 ± 0.02 | w. |

The active catalyst of this type which may be utilized in the process of the present invention, is characterized as an "H-ZSM-5" zeolite and is prepared from a "ZSM-5" zeolite by replacing most, and generally at least about 80% of the cations of the latter zeolite with hydrogen ions using techniques well-known in the art.

Another class of pentasil type silicates which may be utilized as catalysts in the process of this invention are the "silicalites" which are crystalline silica polymorphs, many of which are similar to those described, for example, in previously-cited U.S. Pat. No. 4,061,724, issued to Grose et al on Dec. 7, 1977, the entire disclosure of which is incorporated by reference.

The X-ray powder diffraction pattern of many of the silicalites utilized in the present invention (600° C. calcination in air for one hour) has as its six strongest lines (i.e. interplanar spacings) those set forth in Table III below, wherein "S"=strong and "VS"=very strong.

TABLE III

| d-A | Relative Intensity |
|---|---|
| 11.1 ± 0.2 | VS |
| 10.0 ± 0.2 | VS |
| 3.85 ± 0.07 | VS |
| 3.82 ± 0.07 | S |
| 3.76 ± 0.05 | S |
| 3.72 ± 0.05 | S |

The silicalites utilized as catalysts in the present invention have in the as-synthesized form a specific gravity at 25° C. of 1.99±0.08 g/cc as measured by water displacement. In the calcined (600° C. in air for 1 hour) form silicalite has a specific gravity of 1.70±0.08 g/cc. With respect to the mean refractive index of silicalite crystals, values obtained by measurement of the as-synthesized form and the calcined form (600° C. in air for 1 hour) are, respectively, 1.48±0.01 and 1.39±0.01.

Crystals of silicalite in both the as-synthesized and calcined form are orthorhombic and have the following unit cell parameters: a=20.05 A, b=20.0 A, c=13.4 A, with an accuracy of ±0.1 A on each of the above values. The pore diameter of silicalite is about 5 to 6 Angstrom units and its pore volume is 0.18±0.02 cc./gram as determined by adsorption.

The pores of the silicalite particles have a pattern providing for easy access to vapors and liquids intended to be reacted. For example the pores may be in the form of zig-zag channels cross-linked by straight channels.

The preparation of silicalite may be accomplished, for example by the hydrothermal crystallization of a reaction mixture comprising water, a source of silica and an alkylonium compound at a pH of 10 to 14 to form a hydrous crystalline precursor, and subsequently calcining that precursor to decompose alkylonium moieties present therein. The preparation procedures are described in greater detail in U.S. Pat. No. 4,061,724.

The silicalites contemplated for use in this invention generally contain about 700 to 14,000 ppm of alumina corresponding to a $SiO_2$ to $Al_2O_3$ ratio of about 120 to 2450, preferably about 5000 to 7000 ppm of alumina corresponding to a $SiO_2$ $Al_2O_3$ ratio of about 240 to 340. The amount of alumina in the silicalite will generally depend to a large extent on the source of silica. For example, commercially available silica sols can typically contain from 500 to 700 ppm $Al_2O_3$, whereas fumed silicas can contain from 80 to 2000ppm of $Al_2O_3$. Silicalites containing still larger amounts of alumina may be obtained by using other sources of silica with higher contents of alumina as is well-known in the art.

Still another class of pentasil-type silicates which may be utilized as the catalyst in the process of this invention are crystalline borosilicates as described for example in previously-cited U.S. Pat. No. 4,285,919 of Klotz et al, the entire disclosure of which is incorporated by reference. The foregoing crystalline borosilicate materials, which are identified as AMS-1B borosilicates have a particular X-ray powder diffraction pattern as is shown hereinafter. Such a crystalline borosilicate can generally be characterized, in terms of the mole ratios of oxides, as follows in Expression I:

$0.9 \pm 0.2 M_{2/n}O : B_2O_3 : YSiO_2 : ZH_2O$ (I)

wherein M is at least one cation, n is the valence of the cation, Y is within the range of 4 to about 600, and Z is within the range of 0 to about 160, or more.

In another instance, a crystalline borosilicate can be represented in terms of mole ratios of oxides for the crystalline material not yet activated or calcined at high temperatures as follows in Expression II:

$$0.9 \pm 0.2(WR_2O + [1-W]M_{2/n}O):B_2O_3:YSiO_2:ZH_2O \quad (II)$$

wherein R is an alkylammonium cation, M is at least one cation, n is the valence of the cation M, Y is a value within the range of 4 to about 600, Z is a value within the range of 0 to about 160, and W is a value greater than 0 and less than 1.

In Expression I, M can represent an alkali-metal cation, an alkaline-earth-metal cation, an ammonium cation, an alkylammonium cation, a hydrogen cation, a catalytically-active-metal cation, or mixtures thereof. In Expression II, M can represent an alkali-metal cation, an alkaline-earth-metal cation, an ammonium cation, an alkylammonium cation, a hydrogen cation, a catalytically-active metal cation, or mixtures thereof.

Advantageously, the value for Y falls within the range of 4 to about 500. Suitably, Y is within the range of 4 to about 300; preferably, within the range of about 50 to about 160; and more preferably, within the range of about 80 to about 120.

Suitably, Z is within the range of 0 to about 40.

The original cation "M" in the above expressions can be replaced, at least in part, in accordance with techniques well known in the art by ion exchange with other cations. Preferred replacing cations include tetraalkylammonium cations, metal ions, ammonium ions, hydrogen ions, and mixtures of the above. Particularly preferred cations are those which render the AMS-1B crystalline borosilicate more catalytically active. These materials include hydrogen, rare earth metals, aluminum, and other catalytically active materials and metals known to the art. The catalytically active components can be present in an amount from about 0.05 to about 25 weight percent of the AMS-1B crystalline borosilicate.

Members of the family of AMS-1B crystalline borosilicates possess a specified and distinguishing X-ray powder diffraction pattern, which can be obtained by means of X-ray powder diffraction measurements.

In order to facilitate the reporting of the results obtained, the relative intensities i.e., relative peak heights, were arbitrarily assigned the values shown in Table IV.

TABLE IV

| Relative Peak Height | Assigned Strength |
| --- | --- |
| less than 10 | VW (very weak) |
| 10–19 | W (weak) |
| 20–39 | M (medium) |
| 40–70 | MS (medium strong) |
| greater than 70 | VS (very strong) |

These assigned strengths are used hereinafter.

In the following table, interplanar spacings are represented by "d" and are expressed in terms of Angstrom units (A) or nanometers (nm). The relative intensities are represented by the term "I/Io" and the term "assigned strength" is represented by "A.S.".

The AMS-1B crystalline borosilicates provide an X-ray diffraction pattern comprising the X-ray diffraction lines and assigned strengths as shown in Table V:

TABLE V

| d. A | d. nm | A.S. |
| --- | --- | --- |
| 11.2 ± 0.2 | 1.12 ± 0.02 | W–VS |
| 10.0 ± 0.2 | 1.00 ± 0.02 | W–MS |
| 5.97 ± 0.07 | 0.597 ± 0.007 | W–M |
| 3.82 ± 0.05 | 0.382 ± 0.005 | VS |
| 3.70 ± 0.05 | 0.370 ± 0.005 | MS |
| 3.62 ± 0.05 | 0.362 ± 0.005 | M–MS |
| 2.97 ± 0.02 | 0.297 ± 0.002 | W–M |
| 1.99 ± 0.02 | 0.199 ± 0.002 | VW–M |

By simple regulation of the quantity of boron (represented as $B_2O_3$) in the preparation mixture, it is possible to vary the $SiO_2/B_2O_3$ molar ratio in the final product in a range of about 40 to about 600, or more. In instances where an effort is made to minimize aluminum in the borosilicate crystal structure, the molar ratios of $SiO_2/Al_2O_3$ can easily exceed a ratio of 2000:1 to 3000:1, or more. This ratio is generally only limited by the availability of aluminum-free raw materials.

In general, the surface area of the AMS-1B crystalline borosilicate, as determined by BET surface area analysis, falls within the range of about 300 m²/gm to about 450 m²/gm and the particles of the borosilicate have a maximum diameter, as determined by a scanning electron microscope, of about 2 microns.

Procedures for the preparation of the basic AMS-1B borosilicates and various calcination and ion-exchange techniques are described in greater detail in U.S. Pat. No. 4,285,919.

Examples of lower alkyl- or phenyl-substituted benzenes which are contemplated to be reacted under this invention are, for example toluene, ethylbenzene or biphenyl. Examples of lower alkanoic acids which may be reacted with the substituted benzene are acetic, propionic, n-butyric or isobutyric acid. The preferred reactants are toluene and acetic acid which yield 2-MAP as the preferred product.

The reaction may be carried out in vapor or liquid state under a wide variety of conditions. Reaction temperatures may be employed, for example in the range of about 160° to 350° C., preferably about 200 to 300° C.. The pressure is generally uncritical to the reaction and subatmospheric, atmospheric or superatmospheric pressures may be employed. In most cases, however, the pressure of the reaction will be in the range of about 1 to 30 atmospheres absolute.

Although the reaction consumes one mole of substituted benzene per mole of lower alkanoic acid to produce a mole of 4-substituted phenyl lower alkyl ketone, the actual molar ratio of substituted benzene to alkanoic acid in the feed stream may be varied between wide limits, e.g. from about 100:1 to 1:100. It is preferred however that such ratio be in the range of about 1:20 to 1:1.

If the substituted benzene and lower alkanoic acid are in the vapor state at the reaction temperature, then they can be fed in undiluted state or diluted with a relatively inert carrier gas, such as nitrogen, argon, helium, and the like. Likewise, if the reactants are liquid at the reaction temperature, then they also can be used either alone or with a suitable diluent.

Water may be present in the reactant feed stream and is also a principal by-product of the reaction. If water is utilized its amount can range from about 0.5 mole up to about 2 moles of water per mole of substituted benzene and, preferably, ranges from about 1 to 2 moles of water per mole of substituted benzene feed.

Contact or residence time can also vary widely, depending upon such variables as the lower alkanoic acid, catalyst, reactor temperature and pressure. Typical contact times range from a fraction of a second to more than several hours when a catalyst system other than a fixed bed is used, with preferred contact times, at least for vapor phase reactions, between about 0.5 and 200 seconds.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the pentasil catalyst in conjunction with an inert material such as glass wool to regulate the pressure drop of the ractant stream through the catalyst bed and the contact time of the reactant compounds with the catalyst particles.

The following examples are illustrative embodiments of this invention. Percent conversion is calculated by dividing the moles of total product times 100 by the moles of substituted benzene fed. The selectivity is calculated by dividing the percent conversion to the 4- or 3- substituted phenyl ketone by the percent conversion to the total substituted phenyl ketones.

EXAMPLE 1

The catalyst utilized was an H-ZSM-5 zeolite prepared by replacing with hydrogen ions all but 500 ppm based on the weight of the zeolite of the sodium ions in a sodium aluminosilicate ZSM-5 catalyst prepared in accordance with U.S. Pat. No. 3,702,886, in which the ratio of silica to alumina was about 12. About 5.03 g of this catalyst in conjunction with 1.18 g of glass wool was charged to an oil heated 14 in. tubular reactor having an inside diameter of about ¼ in. The length of the catalyst bed after charging was about 4 ⅛ in.

A feed liquid was prepared by mixing 9.2 g (0.1 mole) of toluene with 60.0 g (1.0 mole) of acetic acid. About 8 ml/hr of the reaction feed liquid was evaporated and charged to the reactor with an average flow of 70 ml/min. of helium carrier gas at a temperature of 250–258° C. and pressures before and after the catalyst bed of 149/148 (before/after) psig to 179/150 psig. The vapor effluent was condensed in an ice cooled trap and collected. After four hours the liquid feed was stopped and the passage of helium carrier gas was continued for another 1½ hours to yield 32.92 g of product condensate. Analysis of the condensate indicated a percent conversion of 5.2% to 4-MAP which was the only methylacetophenone detected.

EXAMPLE 2

The procedure of Example 1 was followed except that about 5.04 g of H-ZSM-5 in conjunction with 1.3g of glass wool was charged to the tube reactor, the feed liquid contained 3.6 g (0.2 mole) of water in addition to the toluene and acetic acid, the average flow of the helium carrier gas was 101.3 ml/min, the temperature was in the range of 243°–250° C., and the pressure before and after the catalyst bed was in the range of 165/164 psig to 158/154 psig. The yield was 35.56g of product condensate which on analysis indicated the percent conversion of toluene to 4-MAP to be 5.0%, with no other methylacetophenones being detected.

EXAMPLE 3

The procedure of Example 1 was followed except that about 5.02 g of H-ZSM-5 in conjunction with 1.21g of glass wood was charged to the tube reactor, about 16 ml/hr of the reaction feed liquid was evaporated and charged to the reactor with an average flow of 44.2 ml/min. of helium carrier gas, the temperature was in the range of 245°–255° C., and the pressure before and after the catalyst bed was in the range of 280/260 psig to 158/133 psig. After three hours the liquid feed was stopped and the passage of helium carrier gas was continued for another 1½ hours to yield 49.95 g of product condensate. Analysis of the condensate indicated the percent conversion of toluene to 4-MAP to be 5.2% with no other methylacetophenones being detected.

EXAMPLE 4

The procedure of Example 1 was followed except that about 5.00 g of H-ZSM-5 in conjunction with 1.21 g of glass wool was charged to the tube reactor, an average flow of 80.2 ml/min. of helium carrier was utilized, the temperature was in the range of 276°–280° C., and the pressure before and after the catalyst bed was in the range of 240/189 psig to 187/180 psig. The yield was 39.32g of product condensate which on analysis indicated a percent conversion of toluene to 4-MAP to be 5.2% with no other methylacetophenones being detected.

Examples 5 thru 7 show that ethylbenzene can be selectively acetylated to 4-ethylacetophenone (4-EAP).

EXAMPLE 5

The procedure of Example 1 was followed except that about 4.90 g of H-ZSM-5 in conjunction with 1.21 g of glass wool was charged to the tube reactor, the feed liquid contained 5.3 g (0.05 mole) of ethylbenzene and 60.0 g (1.0 mole) of acetic acid, the average flow of helium carrier gas was 43.43 ml/min, the liquid feed was evaporated at the rate of about 4 ml/hour into the reactor, the temperature was in the range of 248°–250° C., and the pressure before and after the catalyst bed was in the range of 240/160psig to 136/64 psig. The yield was 18.18 g of product condensate which on analysis indicated the percent conversion of ethylbenzene to 4-EAP to be 2.0%, with no other ethylacetophenones being detected.

EXAMPLE 6

The procedure of Example 5 was followed except that about 4.90 g of H-ZSM-5 in conjunction with 1.17 g of glass wool was charged to the tube reactor, the feed liquid contained 10.6 g (0.1 mole) of ethylbenzene in addition to the 60.0 g (1.0 mole) of acetic acid, the average flow of the helium carrier gas was 101.2 ml/min, the temperature was in the range of 248°–264° C., and the pressure before and after the catalyst bed was in the range of 270/260 psig to 268/260 psig. The yield was 12.27 g of product condensate which on analysis indicated a percent conversion of ethylbenzene to 4-EAP of 4.6% with no other ethylacetophenones being detected.

EXAMPLE 7

The procedure of Example 6 was followed except that about 4.85 g of H-ZSM-5 in conjunction with 1.10 g of glass wool was charged to the tube reactor, the average flow of the helium carrier gas was 119.0 ml/min, the temperature was in the range of 275°/283°

C., and the pressure before and after the catalyst bed was in the range of 255/245 psig to 251/242 psig. The yield was 16.00 g of product condensate which on analysis indicated a percent conversion of ethylbenzene to ethylacetophenones of 7.0%. Based on the total amount of ethylacetophenones produced the selectivity to 4-EAP as 96.0% and to 2-EAP was 4.0%.

Examples 8 thru 10 illustrate the effect of contact time on the product selectivity in the acetylation of toluene.

EXAMPLE 8

The procedure of Example 1 was followed except that about 5.08 g of H-ZSM-5 in conjunction with 1.23 g of glass wool was charged to the tube reactor, and an average flow of 103.33 ml/min. of helium carrier gas was utilized resulting in a contact time of the reactants over the catalyst bed of about 32.7 seconds, the temperature was in the range of 245°-254° C., and the pressure before and after the catalyst bed was in the range of 180/170 psig to 171/160 psig. The yield was 36.35 g of product condensate which on analysis indicated a percent conversion of toluene to 4-MAP of 6.7%, with no other methylacetophenones being detected.

EXAMPLE 9

The procedure of Example 8 was followed except that about 5.04 g of H-ZSM-5 in conjunction with 1.24g of glass wool was charged to the tube reactor, feed liquid was evaporated at a rate of 4 ml/hr. and charged to the reactor with an average flow of 84.0 ml/min. of helium carrier gas resulting in a contact time of the reactants over the catalyst bed of about 47.5 seconds, the temperature was in the range of 250°-252° C., and the pressure before and after the catalyst bed was in the range of 130/120 psig to 124/115 psig. The yield was 15.93 g of product condensate which on analysis indicated a percent conversion of toluene to 4-MAP of 7.9% with no other methylacetophenones being detected.

EXAMPLE 10

The procedure of Example 9 was followed except that about 5.00 g of H-ZSM-5 in conjunction with 1.20 g of glass wool was charged to the tube reactor, a flow of 56.0 ml/min. of helium carrier gas was employed resulting in a contact time of the reactants over the catalyst bed of about 169.0 seconds, the temperature was in the range of 216°-224° C., and the pressure before and after the catalyst bed was in the range of 290/200 psig to 155/99 psig. The yield was 14.43 g of product condensate which on analysis indicated a percent conversion of toluene to 4-MAP of 10.9% with no other methylacetophenones being detected.

Examples 11 thru 18 demonstrate the acetylation of toluene and ethylbenzene can also be carried utilizing as catalyst a silicalite which is a highly siliceous non-acidic pentasil-type material.

The catalyst used was a silicalite sold by Union Carbide Corporation under the designation "S-115." It was prepared as described in U.S. Pat. 4,061,724 and was composed of more than 99 wt. % of silica containing about 6500 to 7000 ppm of alimina such that the $SiO_2$ to $Al_2O_3$ ratio was about 241 and the catalyst contained about 0.03 wt. % of the total of sodium and potassium.

The crystal structure of the silicalite was made up of a tetrahedral framework, which contained a large fraction of five-membered rings of silicon-oxygen tetrahedra. Its channel system was composed of near circular zig-zag channels (free cross-section 5.4±0.2A) cross-linked by elliptical straight channels with a free cross-section of 5.75×5.15 A. Both channels were defined by 10 rings. The X-ray powder diffraction pattern was as defined in Table A of U.S. Pat. No.4,061,724.

Other properties of the silicalite were a pore volume of about 0.19 cc/gm and a crystal density of about 1.76 cc/gm.

EXAMPLE 11

The procedure of Example 1 was followed except that about 5.87 g of "S-115" silicalite in conjunction with 1.15 g of glass wool was charged to the tube reactor, an average flow of 117.3 ml/min. of helium carrier gas was utilized resulting in a contact time of the reactants over the catalyst bed of about 33.3 seconds, the temperature was in the range of 245°-253° C., and the pressure before and after the catalyst bed was in the range of 265/260 psig to 265/259 psig. The yield was 30.38 g of product condensate which on analysis indicated a percent conversion of toluene to all products of 2.8%, with selectivities to 4-MAP Of 57.0%, and to 3-MAP of 5.6%.

EXAMPLE 12

The procedure of Example 1 was followed except that about 5.85 g of "S-115" in conjunction with 1.23 g of glass wool was charged to the tube reactor, an average flow of 122.0 ml/min. of helium carrier gas was employed resulting in a contact time of the reactants over the catalyst bed of about 28.3 seconds, the temperature was in the range of 300°-304° C., and the pressure before and after the catalyst bed was in the range of 255/245 psig to 251/245 psig. The yield was 32.63 g of product condensate which on analysis indicated a percenS conversion of toluene to all products of 5.4%, and selectitities of 4-MAP of 67.0% and to 3-MAP of 10.0%.

EXAMPLE 13

The procedure of Example 1 was followed except that about 5.79 g of "S-115" in conjunction with 1.15 g of glass wool was charged to the tube reactor, the Feed liquid contained 92.0 g (1.0 mole) of toluene and 60.0 (1.0 mole) of acetic acid, an average flow of 84.0 ml/min. of helium carrier gas was utilized resulting in a contact time of the reactants over the catalyst bed of about 40.7 seconds, the temperature was in the range of 293°-305° C., the pressure before and after the catalyst bed was in the range of 260/255 psig to 254/251 psig, the liquid feed was stopped after three hours and the passage of helium carrier gas was continued for another 1½ hours. The yield was 24.68 g of product condensate, analysis of which indicated a percent conversion of toluene to all products of 3.4%, with selectivities to 4-MAP of 78.0%, and to 3-MAP Of 14.0%.

EXAMPLE 14

The procedure of Example 1 was followed except that about 5.98 g of "S-115" in conjunction with 1.17g of glass wool was charged to the tube reactor, the feed liquid contained 23.0 g (0.25 mole) of toluene and 60.0 g (1.0 mole) of acetic acid, an average flow of 283.4 ml/min. of helium carrier gas was utilized resulting in a contact time of the reactants over the catalyst bed of about 11.7 seconds, the temperature was in the range of 297°-304° C., and the pressure before and after the catalyst bed was in the range of 250/240 psig to 114/110 psig. The yield was 33.26 g of product condensate, analysis of which indicated a percent conversion of toluene to all products of 3.2%, with selectivities to 4-MAP of 81.0%, and to 3-MAP of 11.3%.

EXAMPLE 15

The procedure of Examples 1 was followed except that about 8.04 g of "S-115" in conjunction with 1.19 g of glass wool was charged to the tube reactor, the feed liquid contained 10.6 g (0.1 mole) of ethylbenzene and 60.0 g (1.0 mole) of acetic acid, the average flow of the helium carrier gas was 134.4 ml/min, the temperature was in the range of 247°–253° C., and the pressure before and after the catalyst bed was in the range of 250/240 psig to 198/197 psig. The yield was 28.52 g of product condensate, which on analysis indicated a percent conversion of ethylbenzene to ethylacetophenones of 0.9%. Based on the total amount of ethylacetophenones produced the selectivity to 4-EAP was 100.0%.

EXAMPLE 16

The procedure of Example 15 was followed except that about 7.56 g of "S-115" in conjunction with 1.20g of glass wool was charged to the tube reactor, the average flow of the helium carrier gas was 171.3 ml/min, the temperature was in the range of 297°–301° C., and the pressure before and after the catalyst bed was in the range of 205/204 psig to 204/201 psig. The yield was 32.50 g of product condensate, analysis of which indicated a percent conversion of ethylbenzene to ethylacetophenones of 1.6%. Based on the total amount of ethylacetophenones produced the selectivity of 4-EAP was 88.5% and to 3-EAP was 11.5%.

EXAMPLE 17

The procedure of Example 1 was followed except that about 7.50 g of "S-115" in conjunction with 1.20 g of glass wool was charged to the tube reactor, the feed liquid contained 26.5 g (0.25 mole) of ethylbenzene and 60.0 g (1.0 mole) of acetic acid, the average flow of the helium carrier gas was 123.3 ml/min, the temperature was in the range of 300°–305° C., and the pressure before and after the catalyst bed was in the range of 250/230 psig to 192/180 psig. The yield was 25.85 g of product condensate, analysis of which indicated a percent conversion of ethylbenzene to ethylacetophenones of 1.0%. Based on the total amount of ethylacetophenones produced the selectivity to 4-EAP was 85.0% and to 3-EAP was 15.0%.

EXAMPLE 18

The procedure of Example 1 was followed except that about 7.56 g of "S-115" in conjunction with 1.23 g of glass wool was charged to the reactor, the feed liquid contained 106.0 g (1.0 mole) of ethylbenzene and 60.0 g (1.0 mole) of acetic acid, the average flow of the helium carrier gas was 198.3 ml/min, the temperature was in the range of 297°–305° C., and the pressure before and after the catalyst bed was in the range of 240/238 psig to 199/196 psig. The yield was 31.06 g of product condensate which on analysis indicated a percent conversion of ethylbenzene to ethylacetophenones of 2.7. Based on the total amount of ethylacetophenones produced, the selectivity to 4-EAP was 78.4% and to 3-EAP was 13.7%.

I claim:

1. A process for the production of 4-lower alkyl- or 4-phenyl ring-substituted phenyl lower alkyl ketone by reaction of a lower alkyl- or phenyl-substituted benzene with a lower alkanoic acid comprising contacting a feed stream comprising said substituted benzene and acid at an elevated temperature with a medium-pore, pentasil-type molecular sieve as catalyst.

2. The process of claim 1 wherein said catalyst is a ZSM-5 zeolite catalyst having the formula:

$$0.9\pm0.2 M_{2/n}O:W_2O_3:5-100YO_2:zH_2O$$

wherein M is a cation, n is the valence of said cation, W is selected from the group consisting of aluminum and gallium, Y is selected from the group consisting of silicon and germanium, and z is from 0 to 40, and in which at least about 80% of the cations are replaced with hydrogen ions.

3. The process of claim 2 wherein said ZSM-5 zeolite has an X-ray diffraction pattern with lines as shown in Table II of the specification.

4. The process of claim 3 wherein catalyst has the formula:

$$0.9\pm0.2 M_{2/n}O:Al_2O_3:5-100SiO_2:zH_2O$$

and M is selected from the group consisting of alkali metal cations and tetraalkylammonium cations, the alkyl groups of which contain 2–5 carbon atoms.

5. The process of claim 4 wherein the ratio of $SiO_2$ to $Al_2O_3$ in said catalyst is in the range of about 10 to 60.

6. The process of claim 1 wherein said catalyst is a silicalite containing about 700 to 14000 ppm of alumina, which catalyst has been calcined from the as synthesized form at least once.

7. The process of claim 6 wherein said calcined silicalite contains about 5000 to 7000 ppm of alumina.

8. The process of claim 6 wherein said calcined silicalite has a mean refractive index of 1.39±0.01 and a specific gravity at 25° C. of 1.70±0.08.

9. The process of claim 6 wherein the six strongest d-values of the X-ray powder diffraction pattern of said calcined silicalite are as set forth in Table III of the specification.

10. The process of claim 1 wherein said catalyst is an AMS-1B borosilicate.

11. The process of claim 10 wherein said catalyst has the formula $$0.9\pm0.2\ M_{2/n}O:B_2O_3:YSiO_2:ZH_2O \tag{1}$$

wherein M is at least one cation, n is the valence of the cation, Y is within the range of 4 to about 600, and Z is within the range of 0 to about 160.

12. The process of claim 11 wherein the catalyst has an X-ray diffraction pattern as indicated in Tables IV and V of the specification.

13. The process of claim 1 wherein said lower alkanoic acid is acetic acid and said ketone is a lower alkyl or phenyl ring-substituted acetophenone.

14. The process of claim 13 wherein said substituted benzene is toluene and said ketone is 4-methylacetophenone.

15. The process of claim 13 wherein said substituted benzene is ethylbenzene and said ketone is 4-ethylacetophenone.

16. The process of claim 1 wherein said reaction occurs in the vapor phase and said elevated temperature is in the range of about 160° to 350° C.

17. The process of claim 16 wherein said temperature is in the range of about 200° to 300° C.

18. The process of claim 16 wherein said catalyst is in the form of a fixed bed and said feed stream into said bed also contains an inert carrier gas.

19. The process of claim 2 wherein said ketone is 4-methylacetophenone or 4-ethylacetophenone, said substituted benzene is toluene or ethylbenzene, said alkanoic acid is acetic acid, the molar ratio of substituted benzene to alkanoic acid is in the range of about 100:1 to 1:100, the temperature of reaction is in the range of about 160° to 350° degrees C., the pressure of reaction is in the range of about 1 to 30 atmospheres absolute, and the contact time of reactants and catalyst is in the range of about 0.5 to 200 seconds.

20. The process of claim 6 wherein said ketone is 4-methylacetophenone or 4-ethylacetophenone, said substituted benzene is toluene or ethyl benzene, said alkanoic acid is acetic acid, the molar ratio of substituted benzene to alkanoic acid is in the range of about 100:1 to 1:100, the temperature of the reaction is in the range of about 160 to 350 degrees C., the pressure of reaction is in the range of about 1 to 30 atmospheres absolute, and the contact time of reactants and catalyst is in the range of about 0.5 to 200 seconds.

* * * * *